United States Patent [19]
Giarda et al.

[11] Patent Number: 4,632,926
[45] Date of Patent: Dec. 30, 1986

[54] QUINAZOLINONE DERIVATIVES WHICH ARE ACTIVE AGAINST COCCIDIOSIS

[75] Inventors: Silvio Giarda, Novara; Pietro Cesti, Trecate; Giovanni Confalonieri, Monza; Paolo Piccardi, Milan, all of Italy

[73] Assignee: VETEM S.p.A., Milan, Italy

[21] Appl. No.: 511,264

[22] Filed: Jul. 6, 1983

[30] Foreign Application Priority Data

Jul. 6, 1982 [IT] Italy .................. 22245 A/82

[51] Int. Cl.⁴ .................. A61K 31/505; C07D 401/06
[52] U.S. Cl. ....................... 514/259; 544/287
[58] Field of Search .............. 544/287; 424/251; 514/259

[56] References Cited

U.S. PATENT DOCUMENTS

| | | | |
|---|---|---|---|
| 2,320,124 | 5/1967 | Waletzky et al. | 544/287 |
| 2,694,711 | 11/1954 | Baker et al. | 544/287 |
| 4,340,596 | 7/1982 | Schein | 544/287 |
| 4,352,804 | 10/1982 | van Zorge | 544/283 |

FOREIGN PATENT DOCUMENTS

| | | |
|---|---|---|
| 713767 | 8/1954 | United Kingdom ........ 544/287 |
| 2057439 | 4/1981 | United Kingdom . |

OTHER PUBLICATIONS

Lucas, *Organic Chemistry*, Sec. Ed., 1953, American Book Co., New York, pp. 270–271.
Barringer, et al., "J. Org. Chem.", vol. 38, No. 10, 1973, pp. 1933–1940.

*Primary Examiner*—Glennon H. Hollrah
*Assistant Examiner*—James H. Turnipseed

[57] ABSTRACT

There are described compounds of formula:

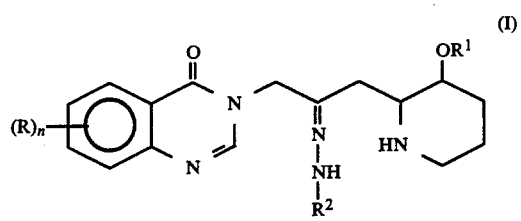

(I)

in which R=alkyl, alkoxy, alkylthio, halogen; n=0, 1 or 2; $R^1$=H, alkyl; $R^2$=H, alkyl, cycloalkyl, phenyl optionally substituted.

The compounds of formula I and the salts thereof are active against the coccidiosis of the domestic and breeding animals, in particular of poultry.

10 Claims, No Drawings

QUINAZOLINONE DERIVATIVES WHICH ARE ACTIVE AGAINST COCCIDIOSIS

BACKGROUND OF INVENTION

U.S. Pat. No. 3,320,124 (American Cyanamid Co.) disclosed the activity against coccidiosis exerted by compounds of formula:

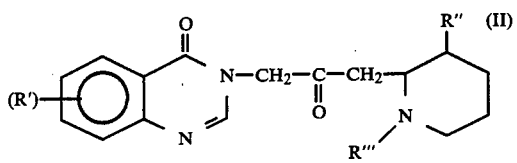

wherein:
R'=H, halogen, nitro, benzo, alkyl, phenyl and alkoxy;
R"=hydroxy, acetoxy and alkoxy;
R'''=H, alkenoxycarbonyl.

The compounds of formula II in which R'''=H, already known as antimalarial compounds (U.S. Pat. No. 2,694,711 American Cyanamid Co.), were obtained by optimization of the antimalarial activity of febrifugine (II, R'=H, R"=OH, R'''=H), a natural alkaloid contained in the inflorescence of Dichroa febrifuga, originally of China and used as antimalarial agent in the pharmacopoeia of said country.

Among the compounds of formula II, the compound commonly known as "Halofuginone" (II, R'=6-Cl, 7-Br; R"=OH; R'''=H) developed by Roussel-Uclaf, proves to be particularly active against coccidiosis in poultry.

Halofuginone possesses a high anticoccidial activity even at very low doses (the practical dose of 3 ppm in the feed is suggested), but it is affected by the drawback of being very toxic for chickens (LD$_{50}$=17.6 mg/Kg). Its low dose of use causes some practical difficulties as, if the admixing to the feed is not perfectly accomplished, the assumption of the product by the chicken may be insufficient, wherefore the animal is not protected from coccidiosis.

On the other hand it is not possible to obviate the risk of under-dosage by excessively increasing the dose of the product because of the toxicity of this toward poultry.

In British Patent Application No. 2,057,439 (Hoechst Co.) there are described some derivatives of the compounds of U.S. Pat. No. 2,694,711 and salts thereof, amongst which also the oxime derivatives. Said compounds are useful in the treatment of theileriasis, a desease of cattle, goats, and sheep which is transmitted by ticks. No anticoccidial activity is disclosed for them.

THE PRESENT INVENTION

We have now found compounds of formula:

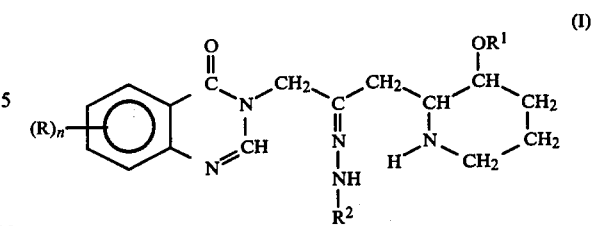

in which:
R is an alkyl $C_1$-$C_4$, an alkoxy $C_1$-$C_4$, an alkylthio $C_1$-$C_4$ or a halogen;
n is zero, one or two;
$R^1$ is a hydrogen atom or an alkyl $C_1$-$C_4$;
$R^2$ is a hydrogen atom, an alkyl $C_1$-$C_8$, a cycloalkyl $C_3$-$C_6$ or a phenyl optionally substituted by one or more alkyl $C_1$-$C_4$ or halogen atoms;
and salts thereof with acids acceptable in the veterinary practice.

The compounds of formula I are endowed with a high anticoccidial activity and a low toxicity towards poultry.

They can be used in the treatment of coccidiosis in domestic and breeding animals, especially birds. Thus, a second object of the present invention is to provide a method for treating coccidiosis consisting in administering to the animals an effective but not toxic amount of a compound of formula I and the anticoccidial compositions to be used in the above said method of treating coccidiosis, which contain a compound of formula I as active ingredient.

The animals subjected to coccidiosis are mainly sheep, cattle, goats, rabbits, swine, but especially birds.

The coccidiosis of poultry, in particular, is one of the most important diseases of these birds with considerable economic losses for breeders because, if not adequately treated, it causes in a short time the death of the animal.

Among the main coccidia which infest birds there may be cited the parasites belonging to the Eimeria genus, species E. tenella, E. acervulina, E. necatrix, E. brunetti, E. maxima and others.

The compounds of formula I are suited to be used in the veterinary field for the treatment of coccidiosis in domestic and breeding animals, in particular in poultry.

In fact, they associate a good anticoccidial activity with a low toxicity toward chickens. Moreover, their anticoccidial activity is both prophylactic and therapeutic thus allowing the prevention as well as the control of coccidiosis.

With respect to Halofuginone, the compounds of the invention are endowed with a comparable anticoccidial activity, some of them being slightly more effective, some others slightly less.

However, the compounds of formula I, are in general, by far less toxic than Halofuginone toward poultry.

Thus, for example, the LD$_{50}$ of Halofuginone is 17.6 mg/Kg body weight while the LD$_{50}$ of some compounds of formula I is about 100 mg/Kg body weight.

Chickens fed with about 38 ppm of Halofuginone in the poultry-feed show phenomena of toxicity while the administration of doses of 64 and 100 ppm of compounds of formula I does not result in any toxicity.

This is a very important feature because in the treatment of coccidiosis in poultry it may often be preferable to have available a compound endowed with a good activity and low toxicity to chickens than an extremely effective compound with a high toxicity.

As herein before mentioned, the possibility of administering a higher dose of an active coccidiostat without the risk of toxicity allows to have an easy and uniform admixture of the compound with the feed so as to avoid the risk of insufficient dosage, in particular in the treatment of poultry coccidiosis.

For practical applications the compounds of formula I are preferably administered to the animal in the form of a preparation or composition.

According to the veterinary practice the preparations or compositions may be in the form of tablets, granules, pellets, pastes, powders, solutions, etc. and contain an effective but not toxic amount of a compound of formula I as active ingredient, an inert solid or liquid carrier such as the common pharmaceutical excipients or a substance of alimentary origin and optionally other additives conventional in the veterinary field.

If desired, it is possible to add to the preparations or compositions other active ingredients useful to the animals health and therapy such as vitamins, antibiotics, anthelmintics, etc.

In the treatment of poultry coccidiosis the anticoccidial compounds of formula I are preferably administered to the animal orally, admixed to the feed or, in the form of salt, dissolved in drinking water.

For oral administration it is convenient to use a composition according to the invention in the form of granules or powder which is intimately admixed with the poultry-feed or co-milled.

The amount of compound of formula I to be given to the animal is determined as a function of different factors such as the kind of animal, the infestation to be controlled, the infestation degree, the selected administration way, the specific effectiveness of the considered compound of formula I, the tolerance of the animal to the considered compound, etc.

Generally, the effective dose for poultry ranges from 0.5 to 2 mg/kg body weight, which corresponds to a dose in the poultry-feed ranging from about 5 to 50 ppm, with reference to the free base.

Higher doses are as well suited, provided they are consistent with toxicity of the product towards the animal.

Specific compounds according to the invention are the compounds of formula I in which n is one or two, substituent R is in position 6 and (or) 7 of the quinazoline moiety and represents an alkyl or a halogen atom, preferably chlorine and bromine.

Likely, specific compounds according to the invention are those in which $R^1$ is hydrogen or methyl and $R^2$ is hydrogen, alkyl or an optionally substituted phenyl with R and n being as above mentioned.

Specific salts of the compounds of formula I are the acid addition salts with physiologically acceptable acids which include mineral acids (hydrogen chloride and hydrogen bromide) and, preferably, weak organic acids (e.g. lactic acid, aceturic acid, citric acid and stearic acid).

The compounds of formula I are the hydrazone derivatives of the corresponding compounds of formula II according to U.S. Pat. No. 2,694,711.

The synthesis of the compounds of formula I is carried out by condensing the suitable compound of formula II (which may be prepared according to the procedure described in the above cited U.S. Patent) with a substantially equimolecular amount of a hydrazine derivative of formula:

$$NH_2-NH-R^2$$

(wherein: $R^2$ has the same meanings as in formula I) or a salt thereof.

To enhance the yields it is useful to use a slight molar excess of the hydrazine derivative.

The condensation may be carried out in an inert polar solvent (e.g. ethanol, dimethylsulphoxide) in the presence of an acid catalyst (e.g. a mineral acid, a buffered system having an acid pH, an acid resin).

We have found that it is particularly convenient to carry out the condensation reaction in an alcohol-water solution in the presence of an acid buffer system, and more particularly in an ethanol-water solution in the presence of a buffer formed by acetic acid and sodium acetate having a pH comprised between 4 and 6.

This method provides higher yields in the desired product and results to be suitable for large scale preparations.

The acid addition salts of the compounds of formula I may be prepared by simply reacting the free base with the selected acid in an inert solvent such as an alcohol.

It has been found that in Halofuginone the trans-isomer in the piperidine ring, i.e. the isomer in which OH group is in trans position with respect to methylene, is endowed with a higher activity than the corresponding cis isomer [see for example D. F. Barringer et al., Journal of Organic Chemistry 38, 1937 (1973)].

It is possible to obtain compounds of formula I in which the trans isomer is the prevailing portion, starting from compounds of formula II already enriched in trans isomer. Such compounds of formula II are preparable according to the method described by D. F. Barringer et al., in Journal of Organic Chemistry 38, 1933 (1973).

The following examples are given to better illustrate the invention.

EXAMPLE 1

Preparation of compound 6-chloro-7-bromo-3-[3-(3-hydroxy-2-piperidyl)-acetonyl]-(3H)-quinazolin-4-one hydrazone

[Compound No. 1] of formula:

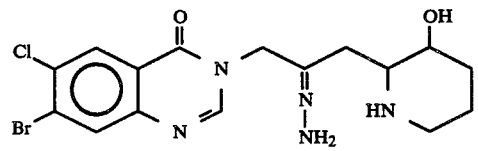

1.8 g of 6-chloro-7-bromo-3-[3-(3-hydroxy-2-piperidyl)-acetonyl]-(3H)-quinazolin-4-one (prepared as described in U.S. Pat. No. 2,694,711) were heated in 200 ml of ethanol until a clear solution was obtained.

To this solution there were added 0.25 ml of hydrated hydrazine in 50 ml of ethanol and 400–500 mg of acid sulphonic resin (the product known under the trademark "Amberlist 15H" was used).

The reaction mixture was heated at a slight reflux for 40 hours. Already after 30–40 minutes it was possible to observe the formation of a product in suspension.

After cooling, the resin was decanted and the solid was separated by filtration and washed with a mixture of ethanol and water in a ratio of about 1:1.

After drying, there were obtained 0.7 g of the desired product as a white solid (melting point=204°-205° C.).

Elemental analysis and $^1$H-NMR spectroscopic data are consistent with the assigned structure.

The infrared spectroscopic data indicate the disappearance of the band at 1720 cm$^{-1}$ ($\nu$C=O) and the presence of a band at 1690 cm$^{-1}$ ($\nu$C=N).

EXAMPLE 2

Preparation of compound 6-chloro-7-bromo-3-[3-(3-methoxy-2-piperidyl)-acetonyl]-(3H)-quinazolin-4-one ethylhydrazone [Compound No. 2] of formula:

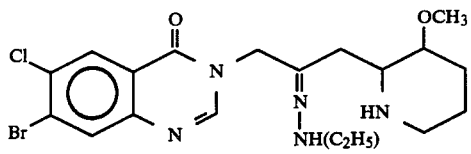

To a solution of 1 g of 6-chloro-7-bromo-3-[3-(3-methoxy-2-piperidyl)-acetonyl]-(3H)-quinazolin-4-one (prepared as described in U.S. Pat. No. 2,694,711) in 200 ml of ethanol, there was added a solution of 0.9 g of ethylhydrazine oxalate and 0.85 g of sodium acetate in 15 ml of water.

The mixture was reflux heated and the reaction course was followed by thin-layer chromatography (alumina layer, solvent: chloroform-methanol in a 9:1 ratio by volume) until only traces of the starting ketone were observed (about 40 hours).

The reaction mixture contained a solid in suspension, which was separated by filtration and washed with ethanol and water in a ratio of about 1:1.

0.3 g of the desired product (white solid, melting point=205°-206° C.) were thus obtained.

The elemental analysis and $^1$H-NMR spectroscopic data are consistent with the assigned structure.

EXAMPLE 3

The compound whose preparation is described in Example 1 (Compound No. 1) was prepared also according to the following procedure:

5 g of 6-chloro-7-bromo-3-[3-(3-hydroxy-2-piperidyl)-acetonyl]-(3H)-quinazolin-4-one were dissolved in a mixture of 50 ml of ethanol and 50 ml of a buffer solution of acetic acid and sodium acetate (pH 6).

2 ml of hydrazine hydrate were added to the solution.

48 hours after the addition, the solvents were eliminated and the residue was treated with a diluted aqueous NaOH solution up to a basic pH.

The undissolved product was collected by filtration thereby obtaining 4.8 g of the desired product, IR and $^1$H-NMR spectroscopic data of which were identical to those of Compound No. 1 (see Example 1).

A sample re-crystallized from methanol showed a melting point of 214° C. with decomposition.

EXAMPLE 4

A large scale preparation of the compound whose preparation is described in Example 1 (Compound No. 1), was carried out as follows:

In an enamelled reactor of 300 l holding capacity equipped with a temperature regulation system and a mechanical stirrer were charged:

100 l of ethanol at 95%;

10 Kg of 6-chloro-7-bromo-3-[3-(3-hydroxy-2-piperidyl)-acetonyl]-(3H)-quinazolin-4-one;

100 l of an aqueous buffer solution (acetic acid-sodium acetate) at pH 4.3.

The mixture was stirred up to obtain a clear solution and 2 l of hydrated hydrazine were added to the solution.

The reaction mixture was stirred at 40° C. The reaction course was followed by analysis (HPLC or TLC) of samples periodically withdrawn from the reactor.

After about 17 hours the starting product (quinazolin-4-one derivative) was present only in traces.

The volatile products (ethanol, water and part of acetic acid) were eliminated under vacuum, they may be collected and used in a subsequent preparation.

The residue was neutralized by the addition of 20 l of water and ice containing 6 Kg of NaOH while the reactor was externally cooled.

The solid precipitate was collected by filtration (filter-press), washed with demineralized water (about 60 l) up to a neutral pH, and dried.

Thereby Compound No. 1 was obtained with 91.5% yield (calculated on the introduced quinazolin-4-one derivative) having the same spectroscopic data as those of the compound prepared as in Example 1 or 3.

EXAMPLE 5

By operating according to the procedure described in Example 3, starting from the suitable quinazolin-4-one derivative and hydrazine derivative, the compounds of formula I reported in the following Table 1 were prepared:

TABLE 1

Compounds of formula[1]

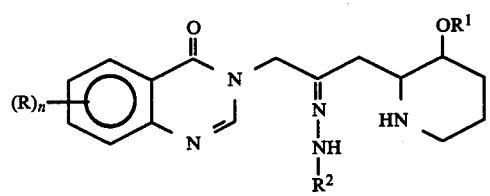 (I)

| Compound No | n | R | R$^1$ | R$^2$ | m.p.[2] (°C.) | IR[3] (cm$^{-1}$) |
|---|---|---|---|---|---|---|
| 1[4] | 2 | 6-Cl, 7-Br | H | H | 214 | 1690, 1600, 1450, 1380, 1310 |
| 2[5] | 2 | 6-Cl, 7-Br | CH$_3$ | C$_2$H$_5$ | 205-6 | 1690, 1590, 1390, 1300 |
| 3 | 2 | 6-Cl, 7-Br | H | C$_6$H$_5$ | — | 1690, 1610, 1500, 1470, 1390, 1320 |
| 4 | 2 | 6-Cl, 7-Br | H | 3-Cl—C$_6$H$_4$ | 201-3 | 1680, 1600, 1450, 1370, 1300 |
| 5 | 2 | 6-Cl, 7-Br | H | 4-CH$_3$—C$_6$H$_4$ | 181-3 | 1680, 1600, 1510, 1440, 1370, 1300, 1270 |

TABLE 1-continued
Compounds of formula[1]

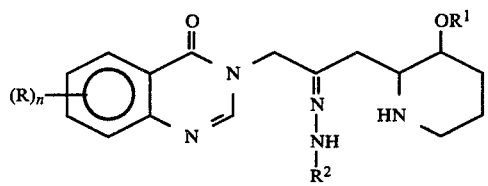

| Compound No | n | R | R[1] | R[2] | m.p.[2] (°C.) | IR[3] (cm$^{-1}$) |
|---|---|---|---|---|---|---|
| 6 | 2 | 6-Cl, 7-Br | H | 2-Cl—C$_6$H$_4$ | 202–3 | 1690, 1600, 1500, 1450, 1370, 1300 |
| 7 | 1 | 6-Cl | H | H | 204–6 | 1690, 1600, 1450, 1380 |
| 8 | 1 | 6-Cl | H | C$_6$H$_5$ | 212–4 | 1690, 1600, 1500, 1390, 1320 |
| 9 | 1 | 6-Cl | H | 3-Cl—C$_6$H$_4$ | 195–7 | 1690, 1590, 1460, 1300 |
| 10 | 1 | 6-Cl | H | 4-CH$_3$—C$_6$H$_4$ | 212–4 | 1680, 1600, 1500, 1430, 1290 |
| 11 | 1 | 6-Cl | H | 2-Cl—C$_6$H$_4$ | 206–7 | 1690, 1600, 1500, 1450, 1300 |
| 12 | 1 | 6-Br | H | H | 217–9 | 1690, 1600, 1490, 1380 |
| 13 | 1 | 6-Br | H | C$_6$H$_5$ | 205–7 | 1680, 1600, 1500, 1390, 1210 |
| 14 | 1 | 6-Br | H | 3-Cl—C$_6$H$_4$ | 199–200 | 1690, 1600, 1500, 1370 |
| 15 | 1 | 6-Br | H | 4-CH$_3$—C$_6$H$_4$ | 194–6 | 1690, 1610, 1490, 1300, 1250 |
| 16 | 1 | 6-Br | H | 2-Cl—C$_6$H$_4$ | 215–7 | 1680, 1600, 1510, 1300 |
| 17 | 1 | 7-Cl | H | H | 200–3 | 1680, 1600, 1450, 1380, 1300 |
| 18 | 1 | 7-Cl | H | C$_6$H$_5$ | 198–200 | 1690, 1600, 1460, 1380, 1300 |
| 19 | 1 | 7-Cl | H | 3-Cl—C$_6$H$_4$ | 209–11 | 1690, 1590, 1500, 1300, 1250 |
| 20 | 1 | 7-Cl | H | 4-CH$_3$—C$_6$H$_4$ | 197–9 | 1680, 1600, 1500, 1370, 1300 |
| 21 | 1 | 7-Cl | H | 2-Cl—C$_6$H$_4$ | 206–8 | 1690, 1600, 1510, 1300 |
| 22 | 1 | 7-Br | H | H | 189–90 | 1690, 1600, 1450, 1300 |
| 23 | 1 | 7-Br | H | C$_6$H$_5$ | 208–10 | 1690, 1600, 1500, 1300 |
| 24 | 1 | 7-Br | H | 3-Cl—C$_6$H$_4$ | 183–5 | 1680, 1590, 1490, 1300, 1240 |
| 25 | 1 | 7-Br | H | 4-CH$_3$—C$_6$H$_4$ | 197–9 | 1690, 1590, 1500, 1300 |
| 26 | 1 | 7-Br | H | 2-Cl—C$_6$H$_4$ | 204–6 | 1680, 1590, 1500, 1290, 1250 |

Notes to Table 1
[1]Elemental analysis and $^1$H—NMR spectroscopic data of all the compounds are consistent with the assigned structure.
[2]m.p. = melting point, the compounds decompose at the indicated temperature.
[3]IR = Infra-red spectroscopic data, meaningful bands only are reported.
[4]The preparation of Compound No. 1 is reported in details in Example 1 or 3.
[5]The preparation of Compound No. 2 is reported in details in Example 2.

EXAMPLE 6
Determination of the coccidiostatic activity in vivo

Groups of 5 one-week-old Ranger pullets were infected each with a mixture of 5500 sporulated oocysts of *Eimeria tenella* and with 5000 sporulated oocysts of *Eimeria acervulina*.

The compound being tested was administered at the preselected dose in admixture with a poultry-feed (LD5) poor in vitamin K and containing no other additive.

The pullets were fed ad libitum with a fodder so prepared, beginning from 1 day prior to the infestation and going on for further 5 days.

As a check, there were used non-infested non-treated chickens and infested non-treated chickens.

The evaluation of the activity on *Eimeria tenella* was accomplished by ascertaining the presence of lesions, if any, 5 days after the infection, while the activity on *Eimeria acervulina* was evaluated by ascertaining the presence of oocysts, if if any, in the excrements 5 days after the infection.

Compounds of the invention tested against *E. tenella* and *E. acervulina* according to the procedure here above described showed a high activity even at very low doses.

For example, Compound No. 2 (see Example 2) shows a complete activity against *E. acervulina* at the dose of 6.25 ppm and a full activity against *E. tenella* at the dose of 12.5 ppm. The same compound, when tested in order to evaluate its toxicity towards poultry, shows a LD$_{50}$ of about 100 mg/Kg body weight. No toxicity phenomena were observed in chickens fed with a poultry-feed containing 100 ppm of Compound No. 2 along the duration of the activity test.

For comparative purposes the anticoccidial activity of the compounds of the following formula may be considered:

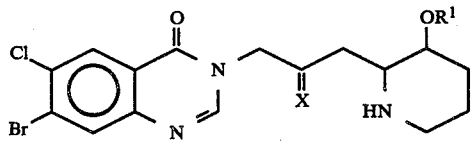

wherein:
a. X is the group =N—OH (hereinafter compound A) which is the free base of a compound according to British Patent Application No. 2,057,439 (oxime derivative of Halofuginone);
b. X is the group =N—NH$_2$ which is Compound No. 1 of Table 1, Example 5;
c. X is the group =N—O—C$_2$H$_5$ (herein after compound B) which is the ethyl-oxime derivative of Halofuginone;
d. X is the group =N—NH—C$_2$H$_5$ which is Compound No. 2 of Table 1, Example 5.

In compounds a, b and c R$^1$ is H, in compound d R$^1$ is CH$_3$.

The above compounds were tested for anticoccidial activity against *E. tenella* and *E. acervulina* according to the procedure hereabove described.

The activity against *E. tenella* was expressed as percent control of the infection at the considered dose, while the activity against *E. acervulina* was expressed on the basis of the presence, if any, of oocysts in the excrements and was rated as follows:

A = absent

M = minimal present

P = present

|  | Dose (ppm) | Compound A | Compound No. 1 |
|---|---|---|---|
| E. tenella | 25 | 100 | 100 |
| (% control) | 12.5 | 40 | 100 |
|  | 6.25 | 0 | 100 |
|  | 3.125 | 0 | 100 |
| E. acervulina | 25 | M | A |
| (oocysts) | 12.5 | P | A |
|  | 6.25 | P | A |
|  | 3.125 | P | M |

|  | Dose (ppm) | Compound B | Compound No. 2 |
|---|---|---|---|
| E. tenella | 25 | completely | 100 |
| (% control) | 12.5 | inactive | 100 |
|  | 6.25 |  | 100 |
| E. acervulina | 25 | completely | A |
| (oocysts) | 12.$ | inactive | A |
|  | 6.25 |  | P |

What we claim is:

1. A compound of formula:

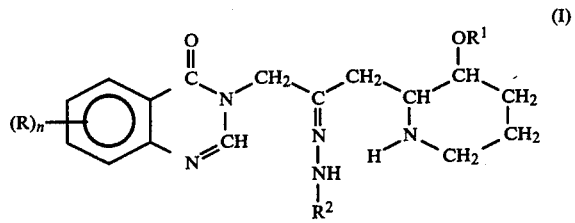

(I)

in which
R is halogen;
n is 1 or 2;
$R^1$ is selected from the group consisting of hydrogen and $C_1$–$C_4$ alkyl;
$R^2$ is selected from the group consisting of hydrogen, $C_1$–$C_8$ alkyl, phenyl substituted by $C_1$–$C_4$ alkyl and phenyl substituted by halogen.

2. A compound according to claim 1, in which $R^1$ is selected from the group consisting of hydrogen and methyl.

3. A compound according to claim 2, in which n is one and R is in position 6 or 7 of the quinazolin-4-one moiety and represents a halogen atom.

4. A compound according to claim 3, in which R is selected from the group consisting of chlorine and bromine atoms.

5. A compound according to claim 2, in which n is 2 and substituents R are in position 6 and 7 of the quinazolin-4-one moiety and represent a halogen atom.

6. A compound according to claim 5, in which substituents R are chlorine and bromine.

7. The compound 6-chloro-7-bromo-3-[3-(3-hydroxy-2-piperidyl)-acetonyl]-(3H)-quinazolin-4-one hydrazone.

8. The compound 6-chloro-7-bromo-3-[3-(3-methoxy-2-piperidyl)-acetonyl]-(3H)-quinazolin-4-one ethylhydrazone.

9. A composition for preventing and controlling coccidiosis in domestic and breeding animals and which comprises an effective, non-toxic amount of a compound according to claim 1.

10. A method of preventing and controlling coccidiosis in domestic and breeding animals consisting in administering to the animals an effective, non-toxic amount of a composition according to claim 9.

* * * * *